United States Patent [19]
Muller et al.

[11] Patent Number: 4,840,634
[45] Date of Patent: Jun. 20, 1989

[54] CALIBRATION CONTROLLER FOR CONTROLLING ELECTRICALLY OPERATED MACHINES

[75] Inventors: Walter Muller, Binningen, Switzerland; Thomas A. Krouskop, Stafford, Tex.

[73] Assignee: Clayton Foundation for Research, Houston, Tex.

[21] Appl. No.: 60,563

[22] Filed: Jun. 10, 1987

[51] Int. Cl.⁴ .............................................. B62D 11/04
[52] U.S. Cl. ................................... 623/24; 280/250.1; 180/6.5; 128/25 R
[58] Field of Search ..................... 128/25 R, 316, 907; 623/24, 25, 26; 180/6.5, 167, 901, DIG. 3; 280/242; 340/825.19

[56] References Cited

U.S. PATENT DOCUMENTS 2,474,200 6/1949 McBee .............................. 128/25 R
2,791,999 5/1957 Bistamanle ........................ 128/25 R
3,769,636 11/1973 Friedman ........................... 128/25 R
4,078,627 3/1978 Brown et al. ....................... 180/6.5
4,260,035 4/1981 Loveless et al. .................... 180/6.5
4,385,541 5/1983 Miller et al. ......................... 84/1.14

OTHER PUBLICATIONS

Lywood, "High-Speed Communication Aid for Quadriplegics", 7/76, Med & Biol. Eng., pp. 445–450.

Primary Examiner—Edward M. Coven
Attorney, Agent, or Firm—Fulbright & Jaworski

[57] ABSTRACT

A controller for enabling a person with limited physical abilities to control one or more electrically operated machines. A movable mouthpiece actuates a pressure transducer in response to blowing or sucking air and a plurality of position transducers are connected to and measure the position of the mouthpiece in a plurality of planes. A controller receives the output of the pressure transducer and position transducers and provides control signals to control one or more machines. The operator can calibrate and adjust the controller to compensate for his/her individual disabilities.

8 Claims, 7 Drawing Sheets

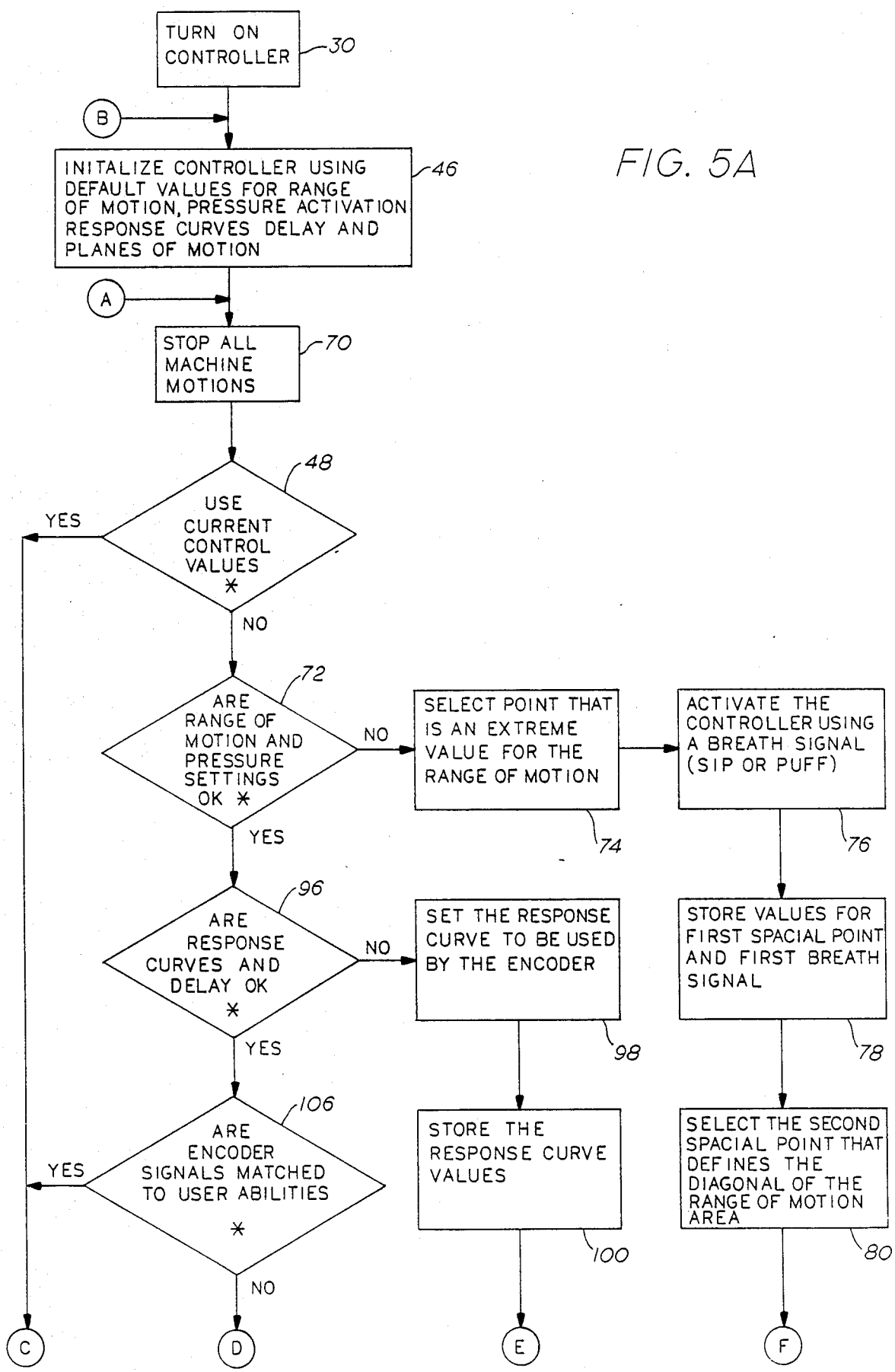

CALIBRATION CONTROLLER FOR CONTROLLING ELECTRICALLY OPERATED MACHINES

BACKGROUND OF THE INVENTION

It is known, as disclosed in U.S. Pat. application Ser. No. 06/592,041, file Mar. 21, 1984, entitled "Devices For Controlling Electrically Operated Appliances", to provide a controller for enabling a person with limited physical abilities to control an electrically operated machine such as a wheelchair or a typewriter. Such devices use a movable mouthpiece which provides an output signal in response to blowing or sucking air therethrough and position transducers connected to the mouthpiece for measuring the position of the mouthpiece in a plurality of planes.

However, persons with limited physical abilities such as a person with a high level of spinal cord injury, have differing capabilities as to their ability to blow or suck air, the extent and direction of their ability to move a mouthpiece, and their response time to control and operate the mouthpiece.

The controller of the present invention allows the operator to adjust and calibrate the controller to compensate for the operator's individual disabilities. The controller provides the advantage of permitting operators to use their available force and motion capabilities to operate an electrically operated machine. In addition, another feature is that the controller provides a single interface that is capable of interacting with more than one electrically operated machine and therefore represents a significant improvement over the many interfaces currently required to control multiple machines. For example, the operator may selectively operate a motorized wheelchair, a personal computer, a robot, or a music synthesizer.

Using the present invention, a person with very limited physical abilities can become adept at operating a wide range of electronic and electrical mechanical equipment. Without such a control system, physically disabled persons have very limited opportunities to perform vocational, leisure, and social activities autonomously.

SUMMARY

The present invention is directed to a controller for enabling a person with limited physical abilities to control one or more electrically operated machines and includes a movable mouthpiece adapted to conduct an air flow therethrough in response to a person's blowing and/or sipping air therethrough. A pressure transducer is connected to the mouthpiece and actuated by air flow through the mouthpiece and provides a signal in response to air flow. A plurality of Position transducers are connected to and measure the position of the mouthpiece in a plurality of planes. Each transducer emits a signal characteristic of the position of the mouthpiece in a particular plane. A controller is connected to and receives the output of the pressure transducer and the position transducers and is connected to and controls one or more machines by control signals. The controller includes calibration means responsive to the outputs of the pressure transducers and the position transducers selecting one or more planes of motions to be used for control, in response to the operator, and selects the range of motion, in response to the operator, in each selected plane to be used for control. The calibration means rearranges the control signals to fit within the selected planes and range of motion. Thus, the controller responds to the person to define the spatial planes in which the mouthpiece will be used, defines the usable area within each plane, and uses the preferred region of operation within each plane.

A still further object is wherein the calibration means includes means for defining one point which is the person limiting value for one extreme value of the person's range of motion in the X, Y and Z directions and a second point which defines the diagonal of the person's range of motion in the X, Y and Z directions and defines the usable range of motion from said first and second points.

Still a further object is wherein the calibration means measures and sets minimum pressure differentials needed, in response to a person's actuation of the mouthpiece, to Provide a signal in response to air flow. This allows the controller to disregard extraneous signals from the operator.

Yet a still further object of the present invention is wherein the controller includes means for providing control signals which vary linearly and/or non-linearly relative to the outputs of the position transducers. The differing responses are used depending upon the sensitivity of the operator's capabilities and/or the functions to be performed.

Still a further object of the present invention is wherein the controller selectively provides output signals for controlling a plurality of electrically operated machines in response to the operator. For example, these may include a motorized wheelchair, robotic device, personal computer, musical synthesizer, or a remote environmental control system.

Yet a still further object is wherein the controller is actuated by a signal that must be maintained for a predetermined amount of time by the person for insuring a response to only a person's desired signal.

Other and further objects, features and advantages will be apparent from the following description of a presently preferred embodiment of the invention, given for the purpose of disclosure and taken in conjunction with the accompanying drawings.

DESCRIPTION OF THE PREFERRED EMBODIMENT

Figure 1:
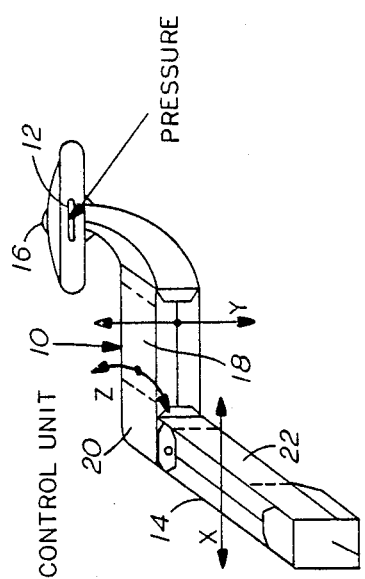
FIG. 1 is a Perspective view illustrating the movable mouthpiece of the present invention which provides a signal in response to air flow and position signals of the position of the mouthpiece in the X, Y and Z planes.

Referring now to the drawings, and particularly to FIG. 1, the reference numeral 10 generally indicates a control unit which is actuated by a physically handicapped person who has the capability of puffing (blowing or positive pressure) and/or sipping (sucking or negative pressure) air through a mouthpiece 12 and moving the mouthpiece 12 in one or more directions. The mouthpiece 12 is mounted on an arm 14 which may be suitably supported adjacent the person's mouth regardless of the position of the person such as sitting, standing or lying down.

By blowing or sucking air through the mouthpiece 12 a pressure transducer 16 is actuated by air flow through the mouthpiece 12 and provides an output signal in response to the air flow.

It is to be noted that the mouthpiece 12 can be moved by the motion of the mouth and head of a person operating the mouthpiece 12. Alternatively, the mouthpiece can be moved by hand and using an air bulb. Hereinafter, swiveling movement to the left and right by the head of a person will be designated as movement in the X direction. Up and down movement of the head and mouth will move the mouthpiece 12 in the Y direction. Movement of the mouthpiece 12 in a forward and back direction will move the mouthpiece in a Z direction. Movement of the mouthpiece 12 in the X, Y and Z directions is measured by position transducers 18, 20 and 22 which may be any suitable type of transducers such as conventional Hall effect transducers. The transducers 18, 20 and 22 each provide an output signal characteristic of the position of the mouthpiece 12 in the planes X, Y and Z direction, respectively.

Figure 2:
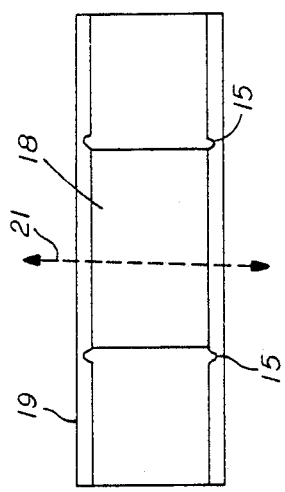
FIG. 2 is an elevational view illustrating the operation of one of the Position transducers.

Referring to FIG. 2, one of the Hall effect transducers 18 is shown which is actuated by movement of its enclosure 19 in the Y direction of arrow 21. Movement about hinge points 15 actuates the transducer 18. Transducers 20 and 22 are similarly actuated by movement in the Z and X direction, respectively.

Figure 3:
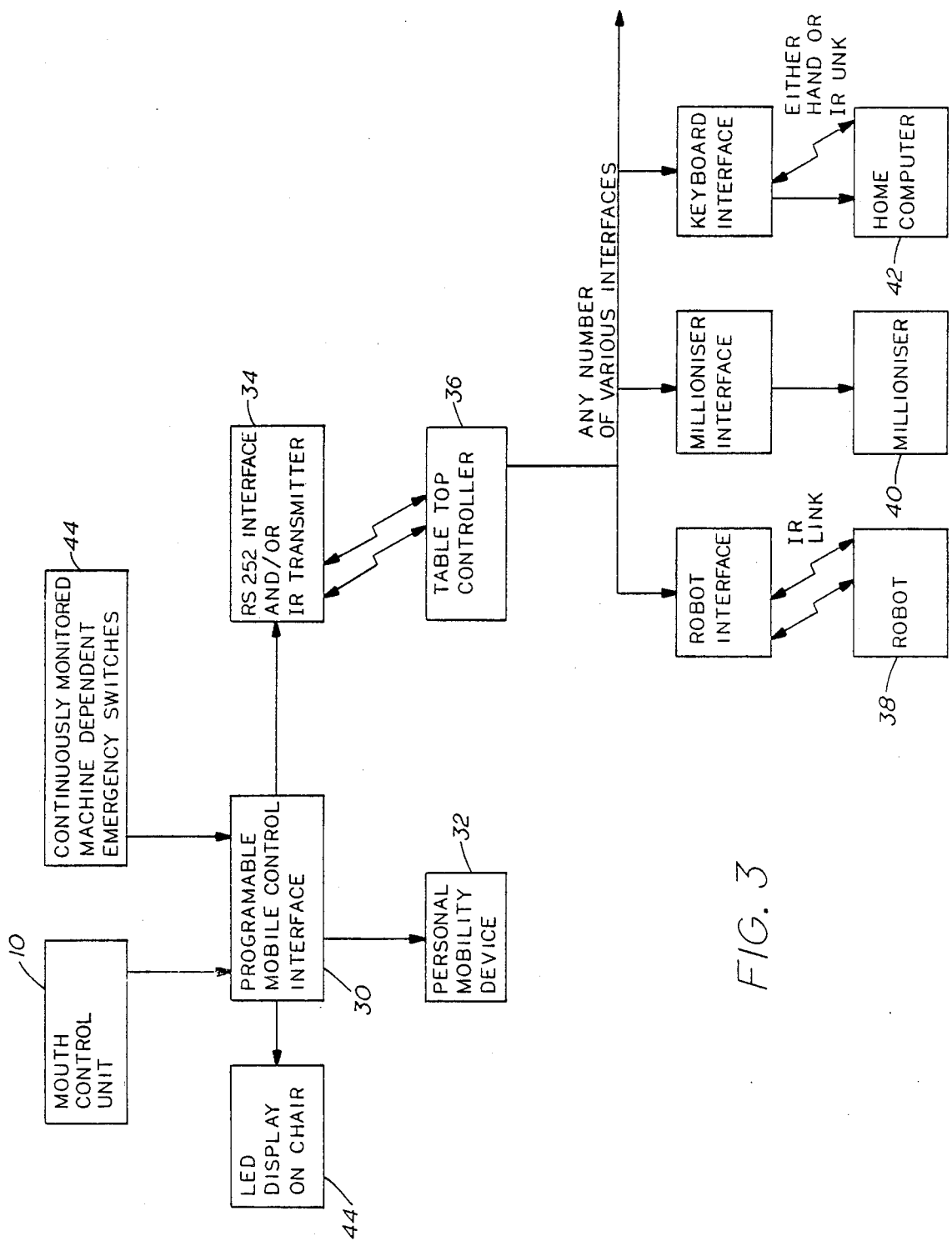
FIG. 3 is an electrical block diagram of the interconnection of the transducer and controller of the present invention for controlling one or more electrically operated machines.

Referring now to FIG. 3, the control unit 10 of the present invention is connected to the programmable controller 30 of the present invention which may control one or more electrically operated devices such as a wheelchair 32 and/or through an RS232 interface and transmitter such as an infrared (IR) transmitter 34 actuates a table top controller 36 which in turn may selectively operate a robot 38, a music synthesizer 40 or a computer 42. The controller 30 may actuate a suitable visual or auditory status module such as an LED display 44. The control unit 10 may include emergency switches 44 for continuously monitoring the wheelchair 32 or robot 38 for stopping the controlled machine in emergencies.

Figure 4:
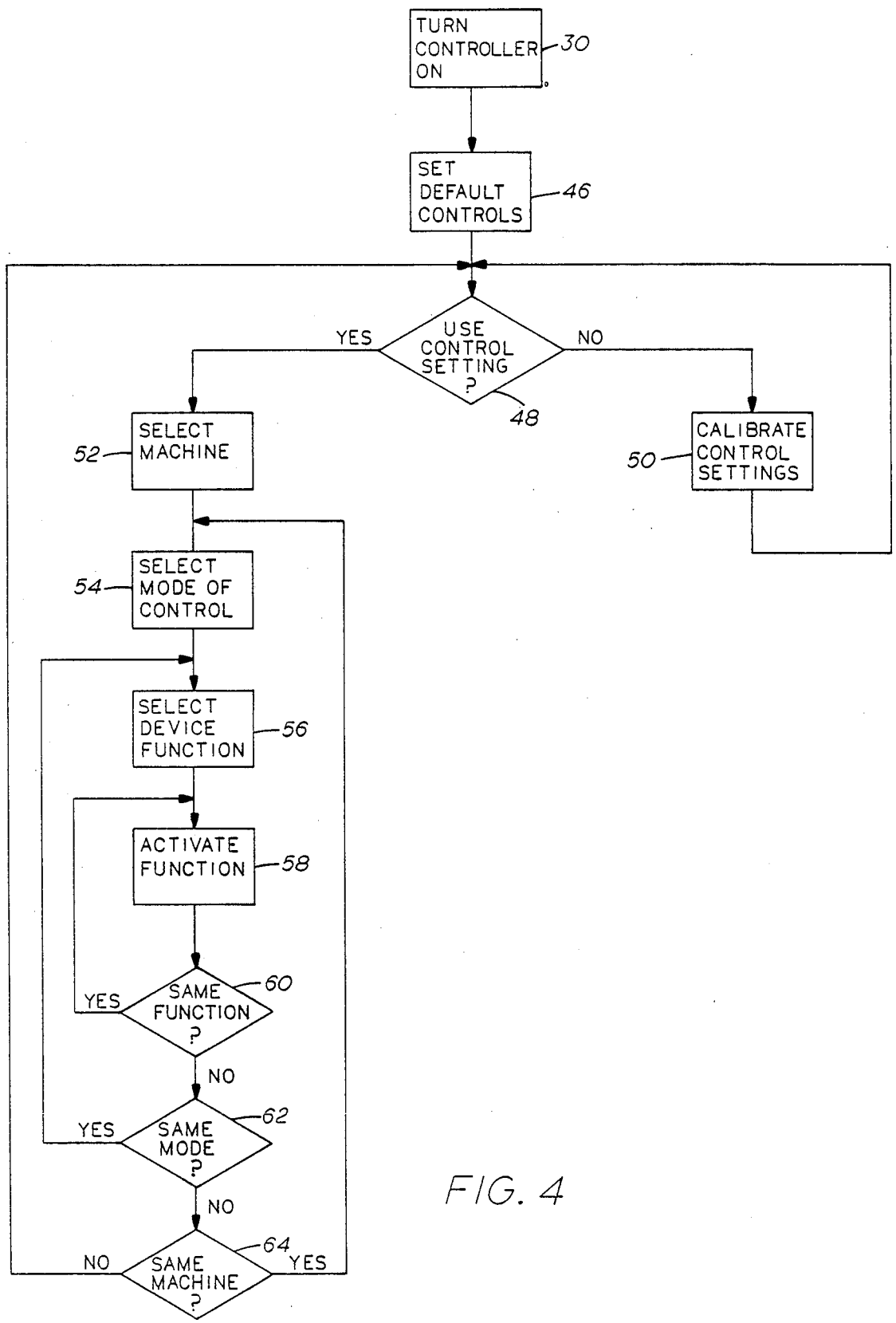
FIG. 4 is an electrical block diagram generally indicating the functional operations of the controller of the present invention, FIGS. 5a and 5b together show a logic flow diagram of the software in the controller, FIG. 6a and 6b together show an operational block diagram of the present invention for controlling a Plurality of electrically operated machines.

Referring now to the operational schematic shown in FIG. 4, the controller 30 is provided with a set of predetermined values or default controls 46 which have been derived from experimental data collected using a number of persons with limited mobility and which represent values that can be achieved by a majority of disabled persons. The predetermined values correlate the output functions of the controller 30 relative to a predetermined range of motion in the X, Y and Z planes, predetermined pressure actuation required for blowing and sucking, predetermined response curves (that is whether the output signal is linearly or non-linearly), and delay time between consecutive signals.

The person or operator makes a decision at control 48 whether to use the predetermined control or default settings or proceed to the calibration step 50, as will be more fully described hereinafter, to adjust the control settings to match his/her individual capabilities.

After the control settings are satisfactory to the person or operator, the operation proceeds to the select machine mode 52 where the person may selectively decide to operate a motorized wheelchair 32, a robotic device 38, a personal computer 42, a musical synthesizer 40 or remote environmental control systems (not shown) such as lights and heat or cooling. After the machine has been selected at operation 52 the operator in step 54 selects the mode of control which will depend upon the electrical machine that is selected to be operated. These controls may include momentary closure devices (keyboard) latched switches (light switch), proportional motion control devices (joystick, mouse or paddle). For example, the operator could use either a keyboard entry, a joystick or a mouse mode of operation for a computer. On the other hand, the control mode for a wheelchair is preferably a joystick type of control mode. By selecting the control mode the controller 30 can generate signals which emulate the selected machine control device. After this, the operator moves to select the device function 56 which, if the wheelchair machine has been selected, the function can be the speed of the wheelchair, or the turning of the wheelchair. If the machine selected at operation 52 is a computer the function could be a letter from the keyboard or if the machine selected in 52 is a robot the function could be a particular motion of the robot.

In operation 58 the selected function is activated using the motion of the mouthpiece 12 or a breath signal and the controller provides a control signal sent to the selected machine for implementation. In operations 60, 62 and 64, the operator selects whether to perform the same function, operate in the same mode, or operate with the same machine, respectively.

Figure 7:
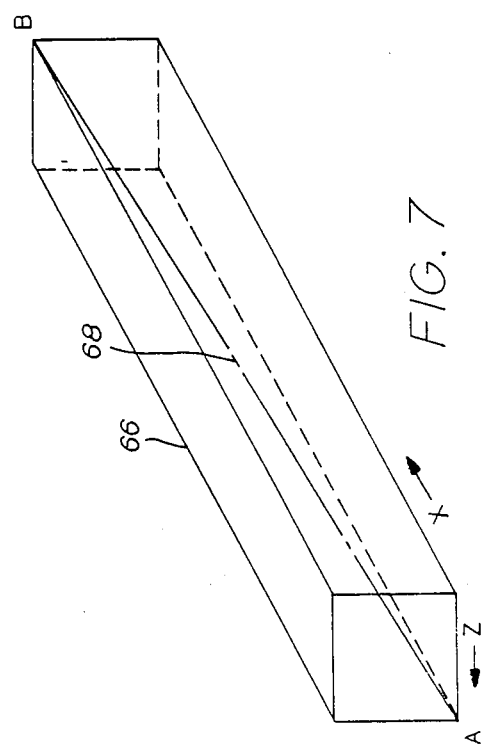
FIG. 7 is a perspective view illustrating the theory of calibration of the controller in response to a person's capabilities.

As previously described, the mouthpiece 12 provides output signals using a breath signal such as sip or puff and also provide movement signals by moving in X, Y and Z directions. Referring now to FIG. 7, the mouthpiece 12 may be moved in X, Y and Z directions to define a Plurality of measurable positions within an area enclosed by a rectangular prism 66 which will define the area in what control functions may be performed by the controller 30. Initially, a set of predetermined or default values for the control variables, such as the range of motion, the planes of motion that are used for control, the pressure differential required to initiate a signal, the response curves and the delay required to cause a signal to be generated, are programmed in the system. These predetermined values have been derived from experimental data collected using a number of persons with limited mobility and capabilities and they represent values that can be achieved by a majority of disabled persons.

However, the person or operator can decide whether to use the preset predetermined control values or whether to recalibrate the controller 30 to tailor match his/her capabilities. In the calibrate mode, the operator may redefine the range of motion. This is accomplished by the operator moving the mouthpiece 32 to define a point A in space, which is one extreme limit of the operator's motion, that represents one end point of a diagonal 68 of the rectangular prism 66. The operator moves the mouthpiece to the operator's limiting value A for that one extreme of the person's range of motion and the operator activates the calibrate system using either a sip or puff breath signal. Once this data is accepted by the controller 30, the operator moves the mouthpiece 12 to the other extreme value of the person's range of motion to define a Point B at the other end of the diagonal 68. The operator uses the opposite breath signal to define the second threshold pressure differential and second spatial point. The location of the end points A and B define the value of the rectangular prism 66 and thus the range of motion of the operator. The sip breath signal at one of the points A is used with the puff breath signal at the other of the points B and is used to define the threshold pressure differentials which the controller will recognize for later control interactions. That is, by measuring the operator's minimum pressure differential needed to activate the pressure transducer 14, the controller 30 uses the breath measurement as a standard for recognizing later control interactions and disregards extraneous movements or pressures which the operator might inadvertently create.

With the measurement of the rectangular prism 66 the controller 30 is thus provided with a measurement of the dimensions of the control space in the X, Y and Z directions which correspond to the range of motion of the particular operator. The controller 30 then fits the number of discrete output control signals into that space and modifies the spacing of the control points and signals to match the individual operator's capabilities.

Figure 8:
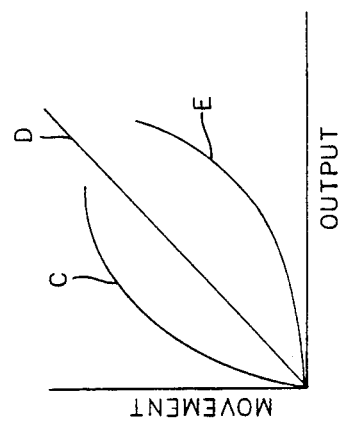
FIG. 8 is a graph illustrating various types of output responses that may be provided for controlling an electrical machine.

Once the controller 30 has measured the range of motion of the operator, the controller also redefines the null point or middle point in the range of motion. That is, the null point is the point where no signal is generated which corresponds to a relaxed or neutral position for the operator. Depending upon the operator's ability and the functions to be performed in the area around the null position, the operator may choose a linear or a non-linear response to changes in the Position of the mouthpiece 12. Referring now to FIG. 8, the operator may choose to select to use various types of output responses such as either the output response represented by the curve C, D or E for various functions. For example, if the operator has very fine control in the area around the null position, non-linear curve C may be chosen which requires only a very small motion of the mouthpiece 12 to change the response and positions near the null point. Conversely, the operator may select response curve E which has little sensitivity around the null point but rapidly increases the sensitivity or response as the mouthpiece 12 is moved further from the null position. Such a response curve would be advantageous in changing the speed or direction of the wheelchair 32 when operating over a rough surface in which the operator is subject to bouncing. The operator also has the option of selecting the linear response curve D.

Figure 5B:
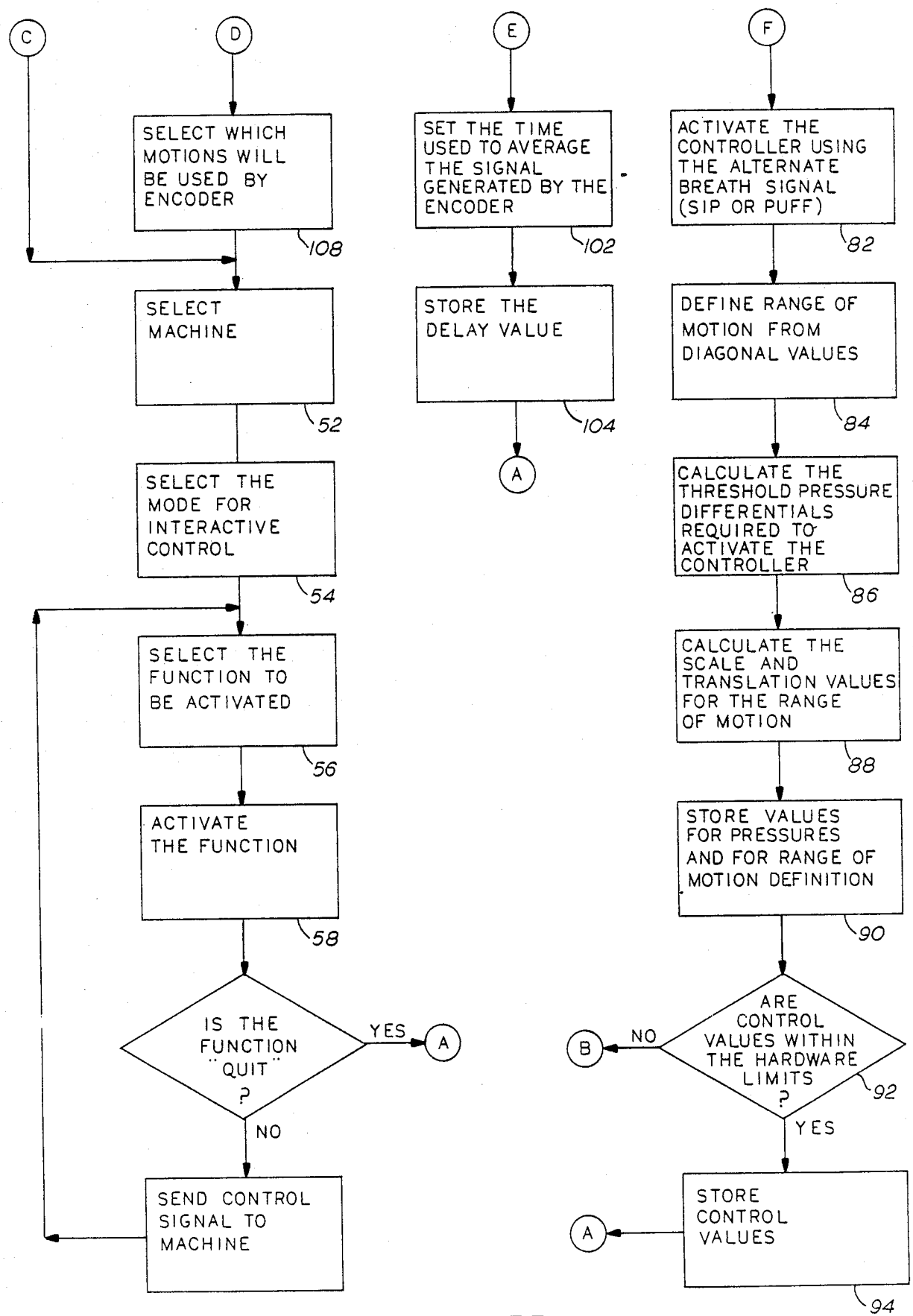

Referring now to FIG. 5, the logic flow diagram of the controller 30 is best seen in combination with its operation. First, the controller 30 is turned on and in step 46 the controller is provided with predetermined or default values for the control variables which represent values that can be achieved by a majority of disabled persons. The predetermined control values include the range of motion of the operator, the Planes of motion that are to be used such as X, Y or Z, the pressure differential required to initiate a signal, the response curves such as shown in FIG. 8 and the time delay required to cause a signal to be generated. At step 70 all machine motions are stopped and in step 48 the operator makes a decision whether or not to use the preset values which are Provided in step 46. If the answer is yes, the operator proceeds with the operation of the machine in step 52 and subsequent steps as previously discussed in FIG. 4. If the answer is no, the operator then proceeds to adjust or calibrate the controller to meet the operator's particular disabilities.

In step 72 the operator decides whether or not the range of motion and pressure settings of the predetermined values are satisfactory. If not, the operator moves to step 74 and moves the mouthpiece 12 to one extreme of the operator's range of motion such as point illustrated in FIG. 7. In step 76 the operator uses a sip or puff signal which defines the one extreme value of the operator's extent of motion and the breath signal is also used to define the threshold pressure differential which the controller 30 will recognize for later control interactions. This data is accepted by the controller 30 in step 78 and the operator moves the mouthpiece 12 to the second extreme value of his motion limit to Point B in step 80. In step 82 he uses the alternate breath signal to that used in step 76 to define a second point B in the X, Y, Z rectangular prism 66 of FIG. 7 which represents the other end point of the diagonal 68 and therefore defines the range of motion that the operator is capable of in the X, Y, and Z planes. These values are used in step 87 by the controller 30 to define the range of motion of the particular operator and in step 86 the controller 30 calculates the threshold pressure differentials required to activate later control signals. In step 88 the controller 30 calculates the scale to be used to fit the number of discrete control signals into the actual dimensions of the measured control space for the operator's personal range of motion. In step 90 the values for the pressures and range of motion are stored, compared in step 92 to determine if the values are within the hardware limits of the apparatus and if yes are stored in step 94.

The operator then returns to step 72 and to decision step 96 in which the operator decides whether the preset values of response curve and delay times are satisfactory. If not, the operator proceeds to step 98 and selects which type of curve, C, D, or E, shown in FIG. 8 which he desires to use for performing the various individual functions of the machine to be selected. In step 100 these values are stored and in step 102 the operator selects a variable period of time in which the operator must maintain a signal before a control signal is sent out by the controller 30 in order to avoid actuating undesired signals. The time delay factor is stored in step 104.

The operator then returns to the calibration mode and proceeds to step 106 to determine which motions are best matched to his particular abilities. For example, even though the operator has defined motions in the X, Y and Z directions, he may feel that one of the directions, such as Z, is incompatible with his ease of operation and in step 108 he will direct the controller 30 that he will only utilize motions in the X and Y directions. This concludes the calibration procedure.

Figure 6A:
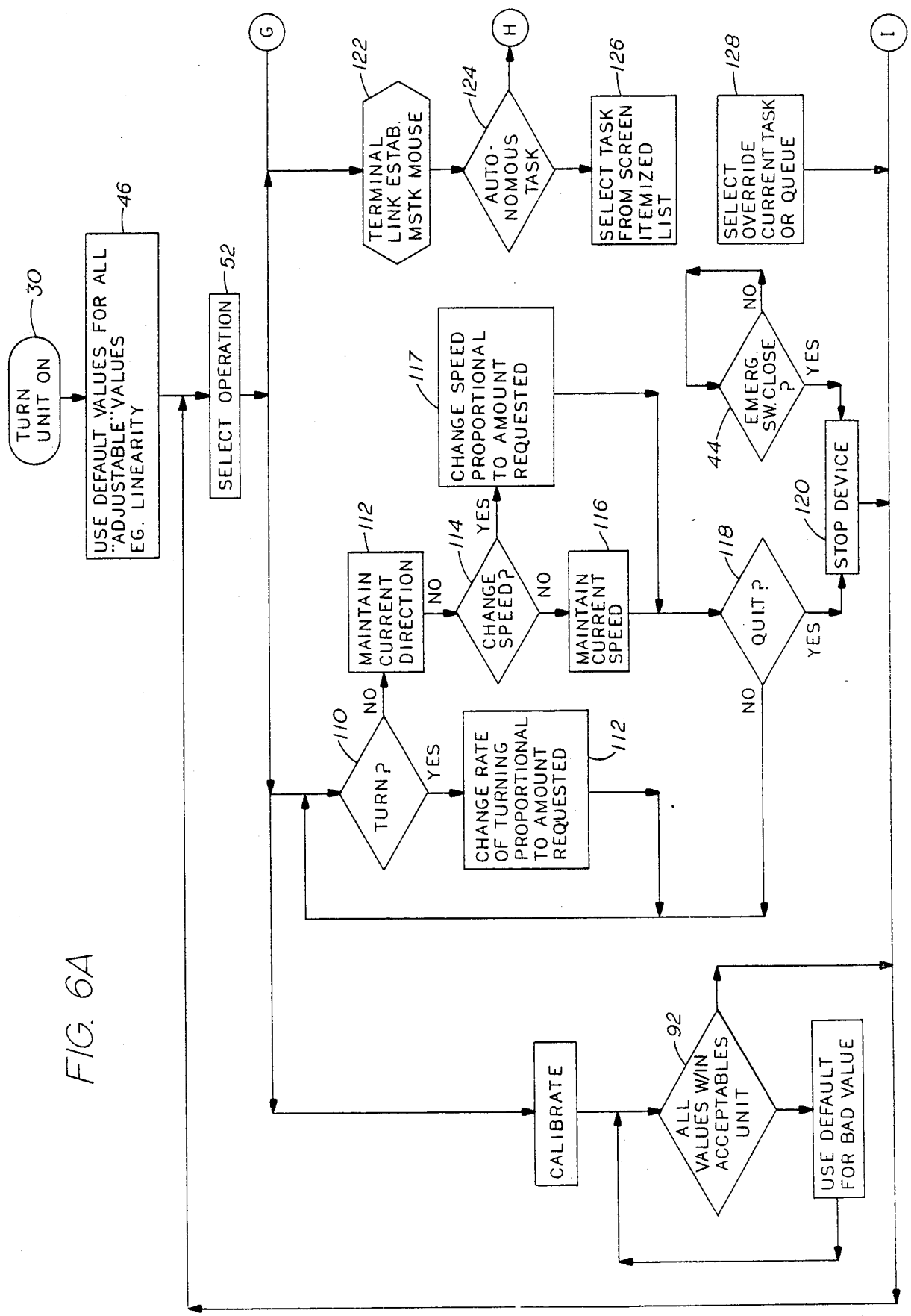
Figure 6B:
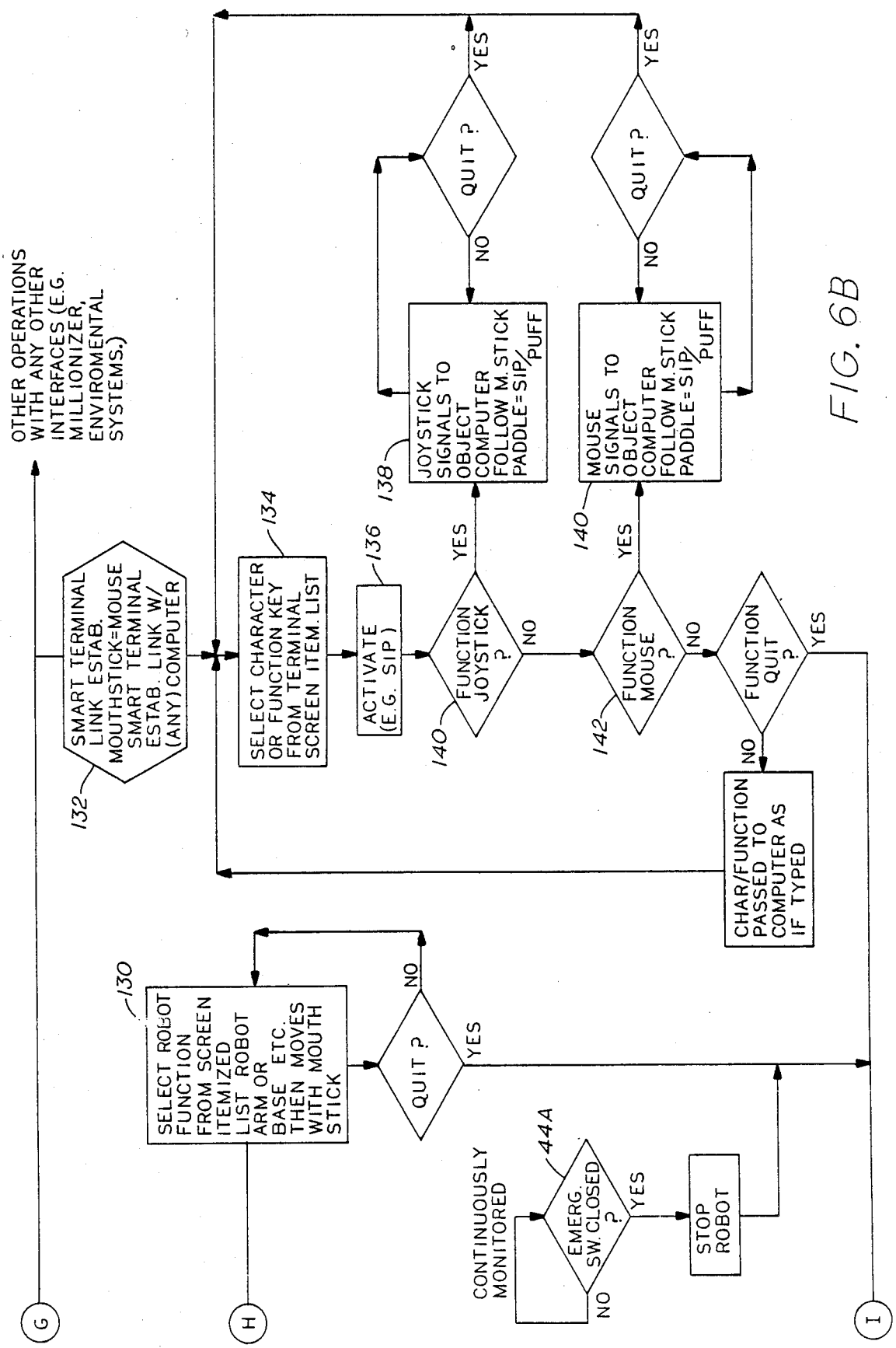

Referring now to FIG. 6, after calibration is completed, the operator proceeds to select one of the machines that he is capable of operating with the controller 30 such as either the mechanized wheelchair 32, a robot 38, a computer 42 or other machines. In operating the wheelchair 32, after selecting the mode of control, the operator selects the function to be performed such as the turn function 110. If a turn is desired, and for example the mode of operation is the movement of the mouthpiece 12, a turn can be provided in step 12 by moving the mouthpiece in one of two directions for controlling the direction of the turn and the amount of the movement determines the degree of the turn. After the turn is completed, the operator returns to step 110 and to step 112 which maintains the current direction and determines in step 114 whether to change the speed of movement of the wheelchair which may be either increased or decreased. If the wheelchair is moving and the speed is satisfactory, the operator proceeds to step 116 to maintain the current speed. If the operator wishes to change the speed, he proceeds to step 117 which changes the speed in proportion to movement of the mouthpiece 12 or to reverse or forward depending upon a different Plane of movement of the mouthpiece 12. The operator then proceeds to step 118 and repeats the cycle for other directions and speed or moves to step 112 to stop the wheelchair.

In controlling a robot 38, the machine is calibrated, the robot machine is selected in operation 52, and a link is established in step 122. If the task to be performed by the robot 32 is autonomous as decided in step 124 the task is selected from a robot screen 126 and proceeds to step 128. If particular tasks are to be performed they are selected in step 130, such as moving the robot arm or base and actuation may be performed by movement of the mouthpiece 12.

In operating a computer 42 a link is established with the computer in step 132 and a character or function key is selected in step 134 from the computer screen and is actuated in step 136 by a sip or puff on the mouthpiece 12. If the computer 138 is actuated by a joy stick, this function is established in step 140 and by motion movement of the mouthpiece 12 the computer follows the mouthpiece 12 and is actuated by a sip or puff on the mouthpiece 12. If a computer 140 is operating with mouth signals, this is accomplished in step 142 to cause the mouse in the computer 140 to follow the motion of the mouthpiece 12 and is actuated by a sip or puff on the mouthpiece 12.

The present invention allows the operator to select motions and forces required to effect control of a machine, allows the operator to define the spatial planes that will be used, allows the operator to define the usable area within each plane and select the preferred region of operation within each plane, and match each desired response curve with a given control motion which may consist of linear and non-linear responses.

The present invention allows the operator to select one or more electronic or electromechanical machines to be controlled and to select control modes to match the selected machines.

The present invention is, therefore, well adapted to carry out the objects and attain the ends and advantages mentioned as well as others inherent therein. While a Preferred embodiment of the invention has been given for the purpose of disclosure, numerous changes in the details of construction and arrangement of parts will readily suggest themselves to those skilled in the art and which are encompassed within the spirit of the invention and the scope of the appended claims.

What is claimed is:

1. A controller for enabling a person with limited physical abilities to control one or more electrically operated machines comprising,
    a movable mouthpiece adapted to conduct an air flow therethrough in response to a person blowing and/or sipping air therethrough,
    a pressure transducer connected to the mouthpiece and actuated by air flow through the mouthpiece, said transducer providing a signal in response to air flow,
    a plurality of position transducers connected to and measuring the position of the mouthpiece in a plurality of planes, each transmitter emitting a signal characteristic of the position of the mouthpiece,
    a controller connected to and receiving the outputs of the pressure transducer and the position transducers and connected to and controlling one or more machines by control signals,
    said controller including calibration means responsive to the outputs of the pressure transducers and the position transducers selecting one or more planes of motion to be used for control in response to the person and selecting the range of motion in response to the person in each selected plane to be used for control, said calibration means arranging the control signals to fit within the selected planes and range of motion.

2. The apparatus of claim 1 wherein the calibration means includes means for defining one point which is the person limiting value for one extreme value of the person's range of motion in the X, Y and Z directions and a second point which defines the diagonal of the person's range of motion in the X, Y and Z direction, and defining the usable range of motion from said first and second points.

3. The apparatus of claim 1 wherein the calibration means measures and sets minimum pressure differentials needed to provide a signal in response to air flow.

4. The apparatus of claim 1 wherein the controller includes means for providing control signals which vary linearly and/or non-linearly relative to the outputs of the position transducers.

5. The apparatus of claim 1 wherein the controller controls a plurality of electrically operated machines.

6. The apparatus of claim 1 wherein the plurality of position transducers measure the position of the mouthpiece in X, Y and Z planes and the controller includes means for controlling the said machines by movement of the mouthpiece in less than all of said planes.

7. The apparatus of claim 1 wherein the controller selectively provides output signals for controlling different types of machine controls.

8. The apparatus of claim 1 wherein the controller is actuated by a predetermined signal time performed by the person.

* * * * *